(12) United States Patent
Dosmann

(10) Patent No.: US 6,181,417 B1
(45) Date of Patent: Jan. 30, 2001

(54) PHOTOMETRIC READHEAD WITH LIGHT-SHAPING PLATE

(75) Inventor: Andrew J. Dosmann, Granger, IN (US)

(73) Assignee: Bayer Corporation, Elkhart, IN (US)

( * ) Notice: Under 35 U.S.C. 154(b), the term of this patent shall be extended for 0 days.

(21) Appl. No.: 09/062,987

(22) Filed: Apr. 20, 1998

(51) Int. Cl.[7] .................................................. G01J 3/28
(52) U.S. Cl. ........................ 356/326; 356/319; 356/320; 356/367
(58) Field of Search .................... 356/326, 367, 356/319, 320

(56) References Cited

U.S. PATENT DOCUMENTS

| | | | |
|---|---|---|---|
| 4,815,848 | * 3/1989 | Hadeishi | 356/326 |
| 4,929,078 | * 5/1990 | Harmon | 356/326 |
| 5,049,487 | 9/1991 | Phillips et al. | 435/4 |
| 5,059,394 | 10/1991 | Phillips et al. | 422/68.1 |
| 5,518,689 | 5/1996 | Dosmann et al. | 422/82.05 |
| 5,611,999 | 3/1997 | Dosmann et al. | 422/82.05 |

OTHER PUBLICATIONS

Physical Optics Corporation "Light Shaping Diffusers" brochure, 2 pages, undated, prior art.

Shie, R. L., et al., article entitled "Surface relief holography for use in display screens", Physical Optics Corporation, 8 pages, undated, prior art.

* cited by examiner

Primary Examiner—Frank G. Font
Assistant Examiner—Reginald A. Ratiff
(74) Attorney, Agent, or Firm—Roger Norman Coe

(57) ABSTRACT

A readhead for a spectrometer for illuminating a target area and receiving light from said target area is provided with a housing adapted to be incorporated in a spectrometer, a light source mounted in a fixed position relative to the housing, a support mechanism adapted to support a biological sample to be illuminated by the light source, a light-shaping mechanism disposed between the light source and the support for increasing the diameter, intensity, and uniformity of the light beam, and a photodetector mounted in fixed position relative to the housing, the photodetector being adapted to detect light from a biological sample disposed in the target area illuminated light sources. The light sources may be in the form of a light-emitting diode that emits substantially monochromatic light having a first wavelength, and the readhead may also include a second light-emitting diode that is adapted to emit substantially monochromatic light of a second wavelength towards the target area.

15 Claims, 2 Drawing Sheets

PHOTOMETRIC READHEAD WITH LIGHT-SHAPING PLATE

BACKGROUND OF THE INVENTION

The present invention relates to a readhead for a photometric diagnostic instrument, such as a reflectance spectrometer, for performing tests on a sample of body fluid to be analyzed.

It is useful for various medical diagnostic purposes to utilize a reflectance spectrometer to analyze samples of body fluid, for example, to detect the blood glucose level of infants. Conventional reflectance spectrometers have been used to detect the presence of glucose in a blood sample disposed on a reagent pad. Glucose present in the blood reacts with the reagent on the reagent pad, causing the reagent pad to change color to an extent which depends on the glucose concentration in the blood.

A readhead for use in a spectrometer device is disclosed in U.S. Pat. Nos. 5,518,689 and 5,611,999 to Andrew Dosmann, et al. That readhead is composed of a housing, a pair of light-emitting diodes fixed relative to the housing and adapted to emit light towards a target area in which a reagent pad is located, and a sensor for detecting light emitted from the illuminated reagent pad.

The accuracy of reagent tests of the type described above is dependent on the sensitivity of the reflectance spectrometer to non-uniform color distributions in the reagent pad. It is desirable that the spectrometer is relatively insensitive to such non-uniform color distributions. It has been realized that two important optical characteristics that minimize inaccuracies caused by non-uniform color development are the size of the reagent area that is read by the instrument and the uniformity of the illumination of the reagent pad.

Some prior art techniques used to attempt to improve the quality of an illumination system include the use of ground glass or frosted Mylar plastic in front of the light source. However, those techniques were tested and found to be unacceptable due to excessive expansion of the light beam, relatively large light output loss, and increased stray light.

OBJECT

It is an object of the invention to overcome the disadvantages of the prior art. This object is solved by a combination of features of the main claim. The subclaims disclose further advantageous embodiments of the invention.

SUMMARY OF THE INVENTION

The summary of the invention does not necessarily describe all necessary features of the invention and the invention may also reside in a sub-combination of described features. The "Summary of the Invention," thus incorporated, presents, therefore, only an example, but not a limitation of the subject matter.

The invention can be summarized as a readhead for a spectrometer for illuminating a target area and receiving light from the target area. The readhead is provided with a housing adapted to be incorporated in a spectrometer, a light source mounted in a fixed position relative to the housing, a support mechanism adapted to support a biological sample to be illuminated by the light source, light-shaping means disposed between the light source and the support for increasing the diameter, intensity and uniformity of the light beam, and a photodetector mounted in fixed position relative to the housing, the photodetector being adapted to detect light from the biological sample illuminated by the light source.

The light source may be in the form of a light-emitting diode that emits substantially monochromatic light having a first wavelength, and the readhead may also include a second light-emitting diode mounted in a fixed position relative to the housing, the second light-emitting diode being adapted to emit substantially monochromatic light of a second wavelength towards the target area, the second wavelength being different from the first wavelength.

The light-shaping means may comprise means for increasing both the uniformity and the divergence of the light beams generated by the light-emitting diodes, and the light-shaping means may be provided in the form of a substantially planar plate that is adapted to transmit greater than about 85 percent all of the light emitted by the light-emitting diodes to the target area. The light-shaping plate may be adapted to cause light from the light-emitting diodes to be distributed in the target area in a Gaussian distribution.

The features and advantages of the present invention will be apparent to those of ordinary skill in the art in view of the detailed description of the preferred embodiment, which is made with reference to the drawings, a brief description of which is provided below.

DETAILED DESCRIPTION OF A PREFERRED EMBODIMENT

Figure 1:
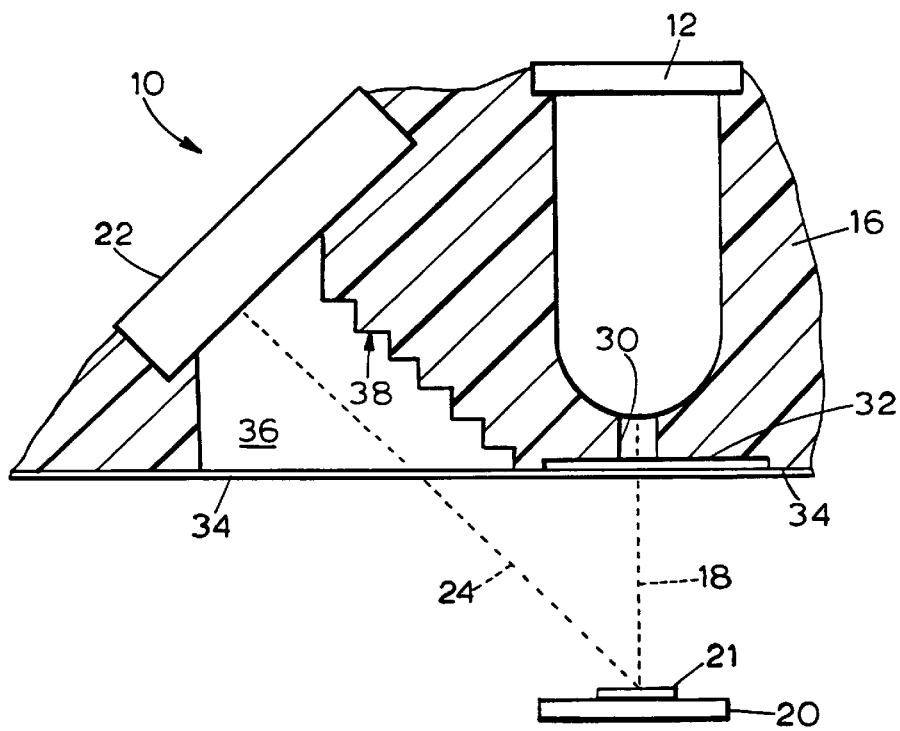
FIG. 1 is a side elevational view, shown partly in cross-section, of a portion of a preferred embodiment of a photometric readhead in accorance with the invention.
Figure 2:
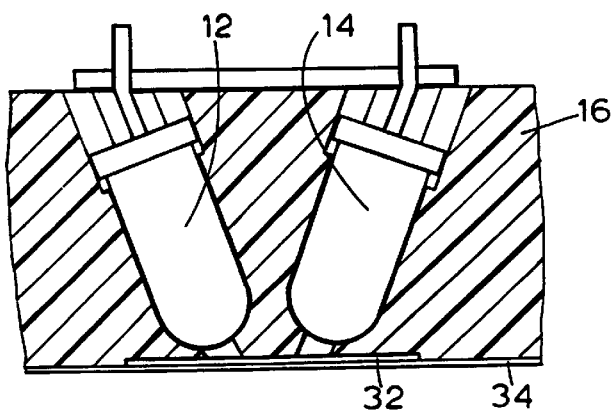
FIG. 2 is front elevational view, shown partly in cross-section, of a portion of the readhead shown in FIG. 1.
Figure 3:
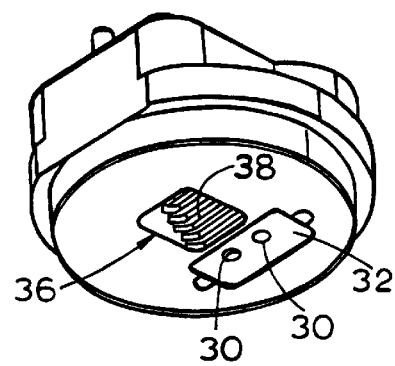
FIG. 3 is an isometric view of the readhead of FIG. 1.

FIGS. 1–3 illustrate a preferred embodiment of a readhead 10 in accordance with the invention. Referring to FIGS. 1–3, the readhead 10 has a pair of light sources in the form of light-emitting diodes (LEDs) 12, 14, each of which is disposed within a housing 16 adapted to be incorporated into a spectrometer.

Each of the LEDs 12, 14 is adapted to emit a substantially monochromatic light beam of a different wavelength, such as red light having a wavelength of about 680 nanometers and infrared light having a wavelength of about 940 nanometers, the light beam being transmitted in a direction indicated by a dotted line 18 shown in FIG. 1. The LEDs 12, 14 are preferably highly directional LEDs, having a 5 degree half power angle.

The LEDs 12, 14 may be activated alternately to illuminate a target area having predetermined dimensions, such as 0.20 inch by 0.20 inch, associated with a support mechanism 20, such as a reagent strip guide, for supporting a sample carrier 21, such as a reagent strip or pad, on which a biological sample to be analyzed is present. Light from the illuminated target area on the sample carrier 21 is detected by a photodetector 22, shown schematically in FIG. 1, which generates an electrical signal indicative of the color of the target area in a conventional manner.

The photodetector 22 is positioned to receive light from the target area on the sample carrier 21 in a direction indicated by dotted line 24. That direction is at a different angle of incidence to the sample carrier 21 from the angle at which the light beams generated by the LEDs 12, 14 are incident on the sample carrier 21, as indicated by dotted line 18, so that the photodector 22 does not receive direct reflections of the light beams generated by the LEDs 12, 14.

The structure of the readhead described above is similar to that of the readhead disclosed in U.S. Pat. Nos. 5,518,689 and 5,611,999 to Andrew Dosmann, et al., the disclosures of which are incorporated herein by reference.

The light beam generated by each of the LEDs 12, 14 passes through a respective one of two relatively small-diameter circular apertures 30 formed in the housing 16, through a substantially planar light-shaping plate 32, and through a window 34, such as polycarbonate, which does not have a substantial effect on the light beam geometry. The light received by the photodetector 22 passes through a reception channel 36 formed in the housing 16. The reception channel 36 has one side in which a staircase baffle 38 is formed so as to reduce the amount of stray light received by the detector 22.

The light-shaping plate 32, which is substantially planar and is relatively thin, e.g., 0.007 inch, performs two primary functions. The plate 32 spreads the light out by increasing the divergence angle of the light beams generated by the LEDs 12, 14 (e.g., from a square beam diameter of 0.0852 inch to a circular beam diameter of 0.140 inch and behaves like a negative lens), and the plate 32 increases the uniformity of the light beams generated by the LEDs 12, 14 (e.g., restructures hot spots into a Gaussian distribution). The light-shaping plate 32 can also transform the overall shape of the light beams generated by the LEDs 12, 14 into other shapes, for example, by transforming the light beams from circular beams to oval-shaped beams which illuminate a rectangular area, or by transforming the light beams from circular beams to line-shaped beams which illuminate a rectangular area having a desired length and a desired width. Similarly, the intensity distribution of the beams can be restructured into a desired distribution, for example a top-hat intensity distribution. The advantages of restructuring the diameter and intensity distribution are provided by the light-shaping plate without regard to the angle of incidence (i.e. both LED beams are restructured by the same plate into identical diameters and intensity distributions even though the two LED angle of incidences are 30° apart). Also, greater than 85% of the incident light is transmitted through the light-shaping plate to the sample carrier 21.

Light-shaping plates like the plate 32 are commercially available from Physical Optics Corporation in Torrance, Calif., which custom manufactures such plates to specifications desired by customers. Such plates are also referred to as "holographic relief plates" or "Light Shaping Diffusers" and are described in further detail in an article by Shie, et al. entitled "Surface Relief Holography for use in Display Screens," which article is incorporated herein by reference.

Figure 4A:
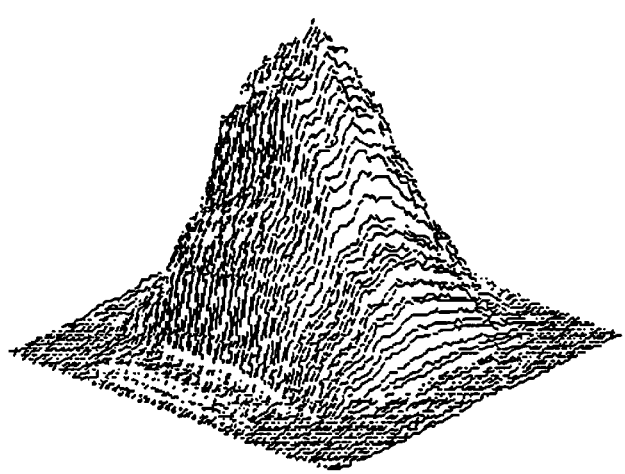
FIG. 4A illustrates the distribution of light generated by a first of the light-emitting diodes of FIG. 1 without the light-shaping plate of FIG. 1.

FIG. 4A illustrates the two-dimensional light distribution generated by a light-emitting diode having a wavelength of 680 nanometers, with the height of the three-dimensional graph representing the light magnitude. It can be seen that the light magnitude does not represent a Gaussian distribution since the light output does not change smoothly as a function of x, y location on the target area, as indicated in particular by the rough peaks and edges in the light output. The light distribution shown in FIG. 4A may have a Gaussian correlation coefficient of between 0.962 and 0.988.

Figure 4B:
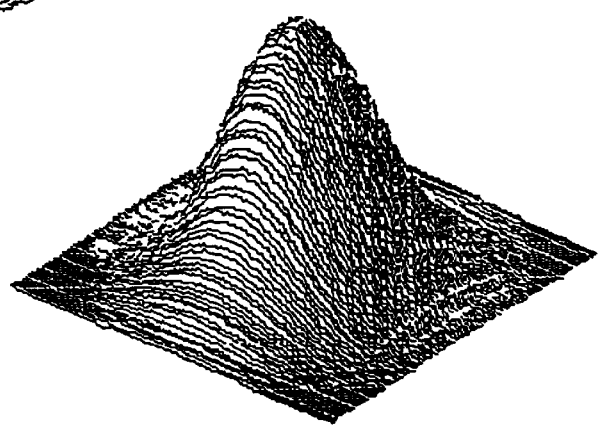
FIG. 4B illustrates the distribution of light generated by the first light-emitting diode of FIG. 1 with the light-shaping plate of FIG. 1.

FIG. 4B illustrates the two-dimensional light distribution generated by the same light-emitting diode as FIG. 4A, except that a light-shaping plate in accordance with the invention has been placed between the light-emitting diode and the target area. The light magnitude of FIG. 4B represents a Gaussian distribution (the light magnitude changes smoothly along the x- and y directions) which has a Gaussian correlation coefficient of between 0.999 and 1.000. A light distribution may be considered a Gaussian distribution if the light distribution has a Gaussian correlation coefficient of 0.995 or above.

Figure 5A:
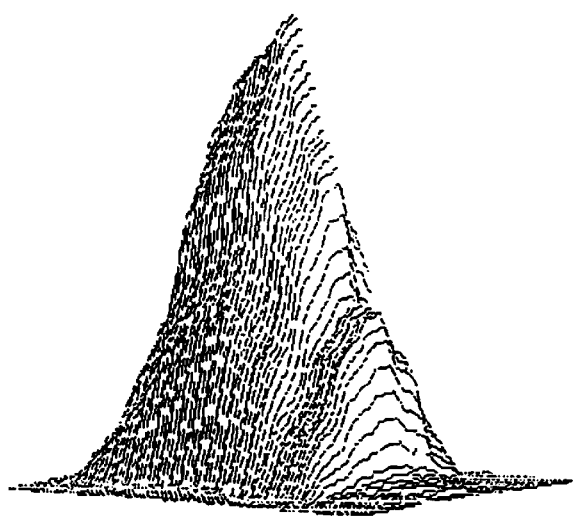
FIG. 5A illustrates the distribution of light generated by a second of the light-emitting diodes of FIG. 1 without the light-shaping plate of FIG. 1.
Figure 5B:
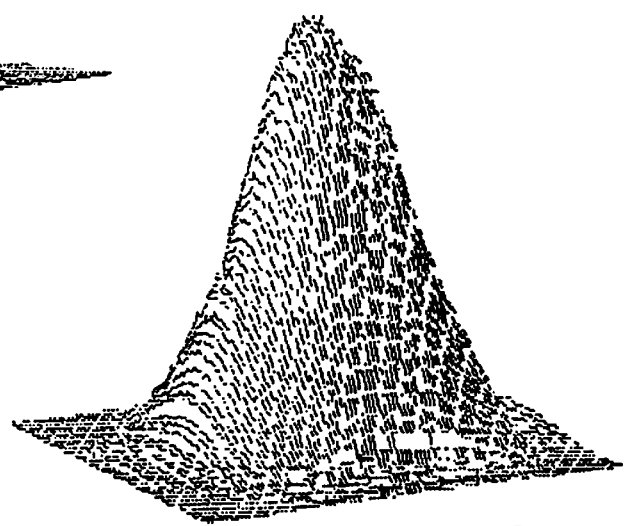
FIG. 5B illustrates the distribution of light generated by the second light-emitting diode of FIG. 1 with the light-shaping plate of FIG. 1.

FIG. 5A illustrates the two-dimensional light distribution generated by a light-emitting diode having a wavelength of 940 nanometers. The light magnitude does not represent a Gaussian distribution since the light output does not change smoothly as a function of x, y location on the target area, as indicated in particular by the rough peaks and edges in the light output. FIG. 5B illustrates the two-dimensional light distribution generated by the same light-emitting diode as FIG. 5A, except that a light-shaping plate in accordance with the invention has been placed between the light-emitting diode and the target area. The light magnitude of FIG. 5B represents a Gaussian distribution.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A readhead for a spectrometer for illuminating a target area having a predetermined area and receiving light from the target area, said readhead comprising:

a housing (16) adapted to be incorporated in a spectrometer;

a first light-emitting diode (12) mounted in a fixed position relative to said housing (16), said first light-emitting diode (12) being adapted to emit a substantially monochromatic light beam having a first wavelength towards said target area, said light beam emitted by said first light-emitting diode (12) having a uniformity and a divergence angle;

a second light-emitting diode (14) mounted in a fixed position relative to said housing (16), said second light-emitting diode (14) being adapted to emit substantially monochromatic light of a second wavelength towards said target area, said second wavelength being different than said first wavelength, said light beam emitted by said second light-emitting diode (14) having a uniformity and a divergence angle;

a support mechanism (20) adapted to support a biological sample to be illuminated by one of said light-emitting diodes (12, 14);

a substantially planar light-shaping plate (32) disposed between said first and second light-emitting diodes (12, 14) and said support mechanism (20), said light-shaping plate (32) being adapted to increase said uniformity of each of said light beams, to increase said divergence angle of each of said light beams, and to transmit greater than about 85 percent of the light emitted by said light-emitting diodes (12, 14) to said target area; and a photodetector (22) mounted in fixed position relative to said housing (16), said photodetector (22) being adapted to detect light from a biological sample disposed in said target area illuminated by one of said light-emitting diodes (12, 14).

2. A readhead as defined in claim 1 wherein said first light-emitting diode (12) is adapted to emit light having a wavelength of about 680 nanometers and wherein said second light-emitting diode (14) is adapted to emit light having a wavelength of about 940 nanometers.

3. A readhead for a spectrometer for illuminating a target area and receiving light from said target area, said readhead comprising:

a housing (16) adapted to be incorporated in a spectrometer;

a first light-emitting diode (12) mounted in a fixed position relative to said housing (16), said first light-emitting diode (12) being adapted to emit a substantially monochromatic light beam having a first wavelength towards said target area, said light beam emitted by said first light-emitting diode (12) having a uniformity;

a second light-emitting diode (14) mounted in a fixed position relative to said housing (16), said second light-emitting diode (14) being adapted to emit substantially monochromatic light of a second wavelength towards said target area, said second wavelength being different than said first wavelength, said light beam emitted by said second light-emitting diode (14) having a uniformity;

a support mechanism (20) adapted to support a biological sample to be illuminated by one of said light-emitting diodes (12, 14);

a light-shaping plate (32) disposed between said first and second light-emitting diodes (12, 14) and said support mechanism (20), said light-shaping plate (32) being adapted to increase said uniformity of each of said light beams so that light from said light beams is distributed in said target area in a Gaussian distribution; and a photodetector (22) mounted in fixed position relative to said housing (16), said photodetector (22) being adapted to detect light from a biological sample disposed in said target area illuminated by one of said light-emitting diodes (12, 14).

4. A readhead as defined in claim 3 wherein said first light-emitting diode (12) is adapted to emit light having a wavelength of about 680 nanometers and wherein said second light-emitting diode (14) is adapted to emit light having a wavelength of about 940 nanometers.

5. A readhead as defined in claim 3 wherein said light-shaping plate (32) is additionally adapted to transmit greater than about 85 percent of the light emitted by said light-emitting diodes (12, 14) into said target area.

6. A readhead as defined in claim 3 wherein said light-shaping plate (32) is additionally adapted to shape said two light beams simultaneously without regard to the angle of incidence of said light beams.

7. A readhead for a spectrometer for illuminating a target area and receiving light from said target area, said readhead comprising:

a housing (16) adapted to be incorporated in a spectrometer;

a light source (12) mounted in a fixed position relative to said housing (16), said light source (12) being adapted to emit a light beam having a uniformity towards said target area;

a support mechanism (20) adapted to support a biological sample to be illuminated by said light source (12);

light-shaping means (32), disposed between said light source (12) and said support mechanism (20), for increasing said uniformity of said light beam; and a photodetector (22) mounted in fixed position relative to said housing (16), said photodetector (22) being adapted to detect light from a biological sample disposed in said target area illuminated by said light source (12).

8. A readhead as defined in claim 7 wherein said light source (12) comprises a light-emitting diode.

9. A readhead as defined in claim 7 wherein said light source (12) comprises a light-emitting diode that emits substantially monochromatic light having a first wavelength.

10. A readhead as defined in claim 9 additionally comprising a second light-emitting diode (14) mounted in a fixed position relative to said housing (16), said second light-emitting diode (14) being adapted to emit substantially monochromatic light of a second wavelength towards said target area, said second wavelength being different than said first wavelength, said light beam emitted by said second light-emitting diode (14) having a uniformity.

11. A readhead as defined in claim 10 wherein said first light-emitting diode (12) is adapted to emit light having a wavelength of about 680 nanometers and wherein said second light-emitting diode (14) is adapted to emit light having a wavelength of about 940 nanometers.

12. A readhead as defined in claim 7 wherein said light beam emitted by said light source (12) has a divergence and wherein said light-shaping means (32) comprises means for increasing said uniformity and said divergence of said light beam.

13. A readhead as defined in claim 7 wherein said light beam emitted by said light source (12) has a divergence, wherein said readhead comprises a second light source (14) mounted in a fixed position relative to said housing (16), said second light source (14) being adapted to emit a light beam towards said target area, said light beam emitted by said second light source (14) having a divergence and a uniformity, and wherein said light-shaping means (32) comprises means for increasing said uniformity and said divergence of said light beams emitted by said light sources (12, 14).

14. A readhead as defined in claim 7 wherein said light-shaping means (32) is additionally adapted to transmit substantially all of the light emitted by said light source (12) into said target area.

15. A readhead as defined in claim 7 wherein said light-shaping means (32) is additionally adapted to cause light from said light beam to be distributed in said target area in a Gaussian distribution.

* * * * *